US012573471B2

(12) United States Patent
Cao et al.

(10) Patent No.: US 12,573,471 B2
(45) Date of Patent: Mar. 10, 2026

(54) METHOD AND DEVICE FOR UROTHELIAL CARCINOMA DETECTION

(71) Applicants: ACORNMED BIOTECHNOLOGY CO., LTD. BEIJING, Beijing (CN); ACORNMED MEDICAL INSTRUMENT CO., LTD. TIANJIN, Tianjin (CN)

(72) Inventors: Shanbo Cao, Beijing (CN); Yafeng Zhang, Beijing (CN); Libin Chen, Beijing (CN); Feng Lou, Beijing (CN)

(73) Assignees: ACORNMED BIOTECHNOLOGY CO., LTD. BEIJING, Beijing (CN); ACORNMED MEDICAL INSTRUMENT CO., LTD. TIANJIN China, Tianjin (CN)

( * ) Notice: Subject to any disclaimer, the term of this patent is extended or adjusted under 35 U.S.C. 154(b) by 0 days.

(21) Appl. No.: 18/760,545

(22) Filed: Jul. 1, 2024

(65) Prior Publication Data

US 2024/0355414 A1 Oct. 24, 2024

Related U.S. Application Data

(63) Continuation of application No. PCT/CN2023/139905, filed on Dec. 19, 2023.

(30) Foreign Application Priority Data

Dec. 30, 2022 (CN) .......................... 202211718465.1

(51) Int. Cl.
*G16B 40/20* (2019.01)
*G16B 20/00* (2019.01)
(Continued)

(52) U.S. Cl.
CPC ............. *G16B 20/00* (2019.02); *G16B 40/20* (2019.02)

(58) Field of Classification Search
CPC ........ G16B 20/00; G16B 40/20; G16B 20/10; G16B 20/20; G06F 18/217; G06F 18/24; G06F 18/253; G16H 30/40; G16H 50/20; G16H 50/30; C12Q 2600/156; C12Q 1/6886
See application file for complete search history.

(56) References Cited

U.S. PATENT DOCUMENTS

2013/0122499 A1 5/2013 Morris et al.
2018/0353073 A1* 12/2018 Boucher .................. A61B 5/05
(Continued)

FOREIGN PATENT DOCUMENTS

CN 108021788 A 5/2018
CN 111833963 A 10/2020
(Continued)

OTHER PUBLICATIONS

China Search Report for Application No. 2022117184651 dated Feb. 7, 2023. Translation provided.
(Continued)

*Primary Examiner* — Brandon S Cole
(74) *Attorney, Agent, or Firm* — Sughrue Mion, PLLC

(57) ABSTRACT

The present disclosure provides a method, a system, a device or an equipment for detecting urothelial carcinoma based on CNV features and/or SNV features.

13 Claims, 5 Drawing Sheets

(51) Int. Cl.

| | | |
|---|---|---|
| *G16B 30/00* | (2019.01) | |
| *G16H 30/40* | (2018.01) | |
| *G16H 50/70* | (2018.01) | |

(56) References Cited

U.S. PATENT DOCUMENTS

| | | | | |
|---|---|---|---|---|
| 2019/0316184 | A1* | 10/2019 | Zimmermann | C12Q 1/6827 |
| 2020/0340064 | A1* | 10/2020 | Gross | G16H 50/20 |
| 2020/0395097 | A1* | 12/2020 | Chang | G16B 25/10 |
| 2021/0090694 | A1* | 3/2021 | Colley | G16B 30/00 |
| 2022/0208305 | A1* | 6/2022 | Bontrager | G16H 15/00 |
| 2022/0336043 | A1 | 10/2022 | Ci et al. | |
| 2022/0372578 | A1 | 11/2022 | Tan et al. | |

FOREIGN PATENT DOCUMENTS

| | | |
|---|---|---|
| CN | 113160889 A | 7/2021 |
| CN | 113257360 A | 8/2021 |
| CN | 115691667 A | 2/2023 |
| WO | 2022203093 A1 | 9/2022 |

OTHER PUBLICATIONS

Li Zhou Min, et al., Clinical Study of Fluorescence in Situ Hybridization in Uroepithelial Tumors, J Contemp Urol Reprod Oncol, Aug. 2014, vol. 6, No. 4. English language translation of abstract is provided.

PCT/CN2023/139905 International Search Report dated Mar. 21, 2024.

* cited by examiner

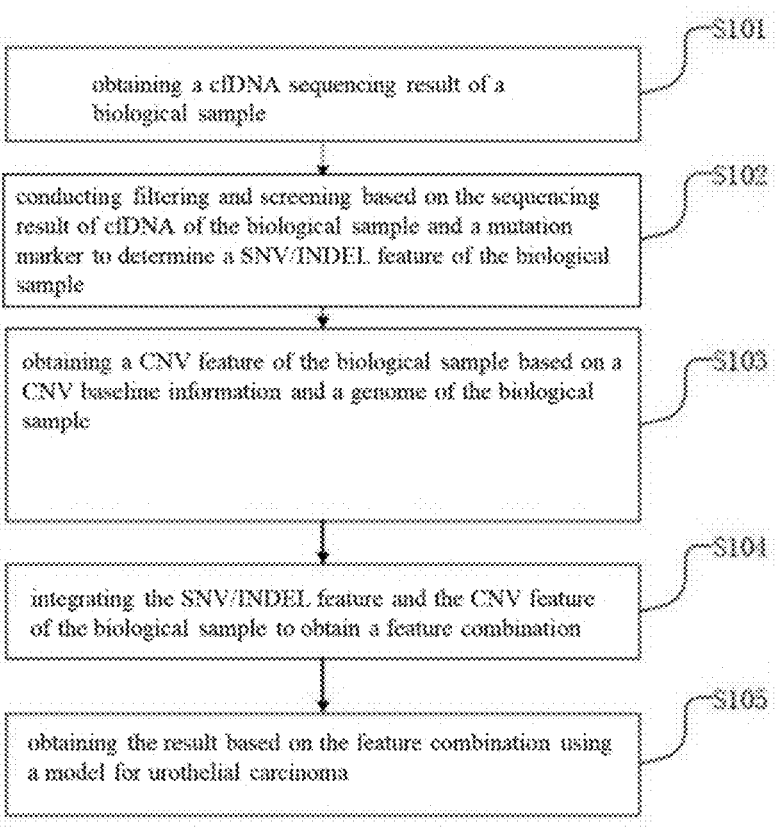

obtaining a cfDNA sequencing result of a
biological sample　　　　　　　　　　　　　　　　S101 conducting filtering and screening based on the sequencing
result of cfDNA of the biological sample and a mutation
marker to determine a SNV/INDEL feature of the biological
sample　　　　　　　　　　　　　　　　　　　　　　S102 obtaining a CNV feature of the biological sample based on a
CNV baseline information and a genome of the biological
sample　　　　　　　　　　　　　　　　　　　　　　S103 integrating the SNV/INDEL feature and the CNV feature
of the biological sample to obtain a feature combination　　S104 obtaining the result based on the feature combination using
a model for urothelial carcinoma　　　　　　　　　　S105

FIG.1

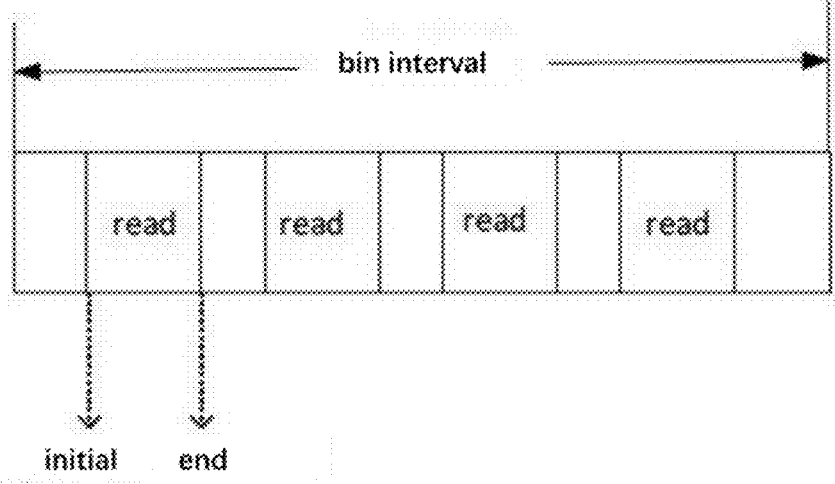

FIG.2

Device for urothelial carcinoma
detection model 300 a second obtaining module — 310 a second mutation screening
module — 320 a second CNV feature
obtaining module — 330 a second feature integrating
module — 340 a model training module — 350 device — 400 processor — 401

402 memory — 403 application
program code transceiver — 404

METHOD AND DEVICE FOR UROTHELIAL CARCINOMA DETECTION

CROSS-REFERENCE TO RELATED APPLICATIONS

This application is a Continuation of and claims priority under 35 U.S.C. § 111 to Patent Cooperation Treaty application PCT/CN2023/139905, filed Dec. 19, 2023, which claims the benefit of Chinese Patent Application No. 202211718465.1, filed Dec. 30, 2022. Priority is claimed to both of these applications and the disclosures of these prior applications are considered part of the disclosure of this application and to the extent allowed the entire contents of the aforementioned applications are incorporated herein.

BACKGROUND OF THE INVENTION

Urothelial carcinoma is a multisource malignant tumor originating from the urothelium, including renal pelvis cancer, ureteral cancer, bladder cancer and urethra cancer. It is the most common urinary system tumor. Urothelial carcinoma is generally divided into non-muscle-invasive and muscle-invasive. The treatment method of non-muscle-invasive urothelial carcinoma comprises surgery, BCG infusion, or chemotherapy. The 5-year survival rate of non-muscle-invasive urothelial carcinoma is 80 to 90% and the patient of non-muscle-invasive urothelial carcinoma usually has a good prognosis. However, if developing into muscle-invasive urothelial carcinoma, the tumor metastasis occurs easily, and the 5-year survival rate is less than 40%. Therefore, a detection and treatment of urothelial carcinoma in an early stage are very important.

At present, the detection methods of urothelial carcinoma include imaging techniques (CT, MRI, urography, B-ultrasound), cystoscopy combined with urine exfoliated cytology and FISH detection, etc. However, the detection rate of ureteral tumors by imaging examinations such as CT and MRI is relatively low, the positive rate of urine exfoliated cytology testing is less than 50%, and urine FISH testing is also subject to specimen conditions and tumor obstruction levels. Furthermore, Ureteroscopy/Flexible endoscopy is an invasive procedure and may increase the risk of bladder metastasis.

Therefore, providing a non-invasive detection with higher detection performance of urothelial carcinoma in an early stage is an urgent problem for those skilled in the art to be solved.

SUMMARY OF THE INVENTION

The present disclosure provides a method, a system, a device or an equipment for detecting urothelial carcinoma based on CNV features and SNV features. Specifically, the method, the system, the device and the equipment of the present disclosure comprises: 1) filtering and screening based on the cfDNA sequencing information and multiple mutation markers of a biological sample of a subject, to determine a SNV/INDEL feature, and 2) obtaining a CNV feature based on a CNV baseline information and a genome of the biological sample, 3) integrating the SNV/INDEL feature and the CNV feature of the biological sample, and 4) determining whether the subject is at a risk for urothelial carcinoma, by using a screening model. The method, the system, the device or the equipment is used for non-invasive cancer detection, and based on the SNV/INDEL feature and CNV feature of a biological sample, and has a high accuracy for urothelial carcinoma, especially for the urothelial carcinoma as an early stage.

The cfDNA sequencing information of more than one biological sample are obtained, wherein the more than one biological sample include a control sample (e.g., a negative sample, a sample from a healthy person.) and a sample from a patient with urothelial carcinoma. For each test sample, the filtering and screening is performed on the basis of the cfDNA sequencing information of the test sample and multiple mutation markers to determine the SNV/INDEL feature; based on the CNV baseline information and the genome of the test sample, CNV feature obtaining is performed to obtain the CNV feature, and then the SNV/INDEL feature and CNV feature corresponding to the test sample are integrated to obtain a feature combination. Then, model training is performed on the basis of all feature combinations corresponding to a large number of test samples to obtain a urothelial carcinoma detection model. Training the model based on a large number of feature combinations can make the screening result more accurate during screening based on the urothelial carcinoma detection model, that is, the sensitivity and specificity are both high.

On one aspect, the present disclosure provides a method for detecting the presence of urothelial carcinoma, assessing the risk of urothelial carcinoma, and/or assessing the prognosis/progression of urothelial carcinoma, the method comprises:

- a) conducting filtering and screening based on a sequencing result of cfDNA of the biological sample and a mutation marker to determine a SNV/INDEL feature of the biological sample, wherein the mutation marker is capable of distinguishing a subject without urothelial carcinoma from a subject with urothelial carcinoma;
- b) obtaining a CNV feature of the biological sample based on a CNV baseline information and a genome of the biological sample optionally the CNV baseline is obtained from more than one samples from the healthy;
- c) integrating the SNV/INDEL feature and the CNV feature of the biological sample to obtain a feature combination; and
- d) obtaining the result based on the feature combination using a model for urothelial carcinoma, wherein the model for urothelial carcinoma is trained using more than one training examples.

In some embodiments, the SNV/INDEL features comprises a mutation number, a mutation label, and/or a maximum mutation frequency.

In some embodiments, the CNV baseline information comprises expected read coverage and standard deviation of each bin interval, and the CNV feature comprises a CNV number and/or a CNV marker.

In some embodiments, b) comprises:

- b1-1) obtaining a segment CNV score of more than one segments of the genome of the biological sample based on the CNV baseline information and the genome of the biological sample;
- b1-2) determining a chromosome CNV score of each chromosome in the biological sample based on the segment CNV score;
- b1-3) for the chromosome CNV score of each chromosome in the biological sample, comparing the absolute value of the chromosome CNV score and a first threshold; if the absolute value of the chromosome CNV score is greater than the first threshold, the CNV marker corresponding to the chromosome is determined to be a positive mark; if the absolute value of the chromosome CNV score is not greater than the first threshold, the CNV mark of the chromosome is determined to be a negative mark;

b1-4) obtaining a first CNV number, wherein the first CNV number is the number of positive markers among all chromosomes;

b1-5) determining the CNV feature based on the first CNV number.

In some embodiments, b) comprises:

b2-1) providing a tumor cell content of the biological sample, and b2-2) determining a second CNV number based on the relationship between the tumor cell content and a second threshold.

In some embodiments, b) comprises:

b3-1) for each segment of each chromosome in the biological sample, if the absolute value of the segment CNV score is greater than a third threshold, the segment is recorded as a CNV interval;

b3-2) for each chromosome in the biological sample, determining the feature ratio based on the CNV interval, wherein the feature ratio is the ratio of the length of all the CNV intervals to the length of the chromosome;

b3-3) for each chromosome in the biological sample, comparing the feature ratio and a fourth threshold, if the feature ratio is greater than the fourth threshold, the CNV mark is determined to be a positive mark, and if the feature ratio is not greater than the fourth threshold, the CNV mark is determined to be a negative mark;

b3-4) obtaining a third CNV number, wherein the third CNV number is the number of positive markers among all chromosomes.

In some embodiments, b1-5) comprises:

determining the CNV number based on the first CNV number and the target CNV number, wherein the target CNV number is the second CNV number and/or the third CNV number; and determining the CNV feature based on the CNV number.

In some embodiments, the b1-1) comprises:

determining a CNV score of each bin interval in the genome of the biological sample based on the CNV baseline information and the genome of the biological sample, wherein the CNV score is for reflecting the difference between the bin interval in the biological sample and the corresponding bin interval in the CNV baseline information; and merging the interval based on the CNV score of each bin interval in the genome of the biological sample to obtain the segment CNV score of multiple sections corresponding to the genome of the biological sample, wherein the section is obtained by continuous bin interval merging.

In some embodiments, the method comprises providing the CNV baseline information before b), which comprises:

1) obtaining the genomes of more than one samples from the healthy;

2) for each sample from the healthy, conducting the CNV sliding window coverage calculation based on the genome of the sample from the healthy to obtain the read coverage of each bin interval in the genome of the samples from the healthy;

3) determining the CNV baseline information based on the read coverage of each bin interval, wherein the CNV baseline information comprises: the expected read coverage and the standard deviation of each bin interval, wherein, the expected read coverage is determined by averaging the read coverages of all samples from the healthy in each bin interval, and the read standard deviation is determined by calculating the variance of the read coverages of all samples from the healthy in each interval.

In some embodiments, the method further comprises for each sample from the healthy, dividing the genome of the sample from the healthy into more than one bin intervals;

for each bin interval, collecting the sum of the number of reads whose start position or end position is located in the bin interval to obtain an initial read coverage of each bin interval;

for each bin interval, conducting GC correction and self-standardization based on the initial read coverage to obtain the read coverage of each bin interval in the genome of the sample from the healthy.

In some embodiments, the mutation marker is determined by filtering and screening mutation sites based on public tumor data, internal samples and sequencing data sets.

In some embodiments, the mutation marker comprising: a mutation of TERT, a mutation of FGFR3 and/or a mutation of ERBB2.

In some embodiments, the mutation marker is selected from the group consisting of: TERT chr5: 1295228-1295228, TERT chr5: 1295250-1295250, FGFR3 chr4: 1803564-1803564, FGFR3 chr4: 1803568-1803568, FGFR3 chr4: 1807890-1807890, FGFR3 chr4: 1807889-1807889, FGFR3 chr4: 1806099-1806099, FGFR3 chr4: 1806092-1806092, FGFR3 chr4: 1806089-1806089, and FGFR3 chr4: 1808937-1808937.

In some embodiments, the mutation marker comprises:

TERT chr5: 1295228-1295228, FGFR3 chr4: 1803564-1803564, TERT chr5: 1295250-1295250, FGFR3 chr4: 1803568-1803568, ERBB2 chr17: 37868208-37868208, and/or FGFR3 chr4: 1806099-1806099.

In some embodiments, the mutation marker comprises:

TERT c.-124G>A, FGFR3 c.742C>T, TERT c.-146G>A, FGFR3 c.746C>G, ERBB2 c.929C>T, and/or FGFR3 c.1118A>G.

On one aspect, the present disclosure provides a method for detecting the presence of urothelial carcinoma, assessing the risk of urothelial carcinoma, and/or assessing the prognosis/progression of urothelial carcinoma, the method comprises:

a) obtaining a CNV feature of the biological sample based on a CNV baseline information and a genome of the biological sample optionally the CNV baseline is obtained from more than one samples from the healthy; wherein a) comprises:

a1) providing a tumor cell content of the biological sample, a2) determining a second CNV number based on the relationship between the tumor cell content and a second threshold, a3) for each segment of each chromosome in the biological sample, if the absolute value of the segment CNV score is greater than a third threshold, the segment is recorded as a CNV interval; and a4) for each chromosome in the biological sample, determining the feature ratio based on the CNV interval, wherein the feature ratio is the ratio of the length of all the CNV intervals to the length of the chromosome.

b) obtaining the result based on the CNV feature using a model for urothelial carcinoma, wherein the model for urothelial carcinoma is trained using more than one training examples.

In some embodiments, the method further comprises:

for each chromosome in the biological sample, comparing the feature ratio and a fourth threshold, if the feature ratio is greater than the fourth threshold, the CNV mark is determined to be a positive mark, and if the feature ratio is not greater than the fourth threshold, the CNV mark is determined to be a negative mark;

obtaining a third CNV number, wherein the third CNV number is the number of positive markers among all chromosomes.

On one aspect, the present disclosure provides a method or detecting the presence of urothelial carcinoma, assessing the risk of urothelial carcinoma, and/or assessing the prognosis/progression of urothelial carcinoma, the method comprises detecting a mutation marker in a biological sample, wherein the gene mutation is selected from the group consisting of: TERT chr5: 1295228-1295228, FGFR3 chr4: 1803564-1803564, TERT chr5: 1295250-1295250, FGFR3 chr4: 1803568-1803568, ERBB2 chr17: 37868208-37868208, and/or FGFR3 chr4: 1806099-1806099.

In some embodiments, the mutation marker comprises:

TERT c.-124G>A, FGFR3 c.742C>T, TERT c.-146G>A, FGFR3 c.746C>G, ERBB2 c.929C>T, and/or FGFR3 c.1118A>G.

On one aspect, the present disclosure provides a device for detecting the presence of urothelial carcinoma, assessing the risk of urothelial carcinoma, and/or assessing the prognosis/progression of urothelial carcinoma, wherein the device is for conducting the method of the present disclosure.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWING

The novel features of the invention are set forth with particularity in the appended claims. A better understanding of the features and advantages of the present invention will be obtained by reference to the following detailed description that sets forth illustrative embodiments, in which the principles of the invention are employed, and the accompanying drawings (also "figure" and "FIG." herein), of which:

FIG. 1 illustrates a schematic flow chart of a method for detection of urothelial carcinoma according to an embodiment of the present application.

FIG. 2 illustrates a schematic structural diagram of calculating an initial read coverage of each bin according to an embodiment of the present application.

Figure 3:
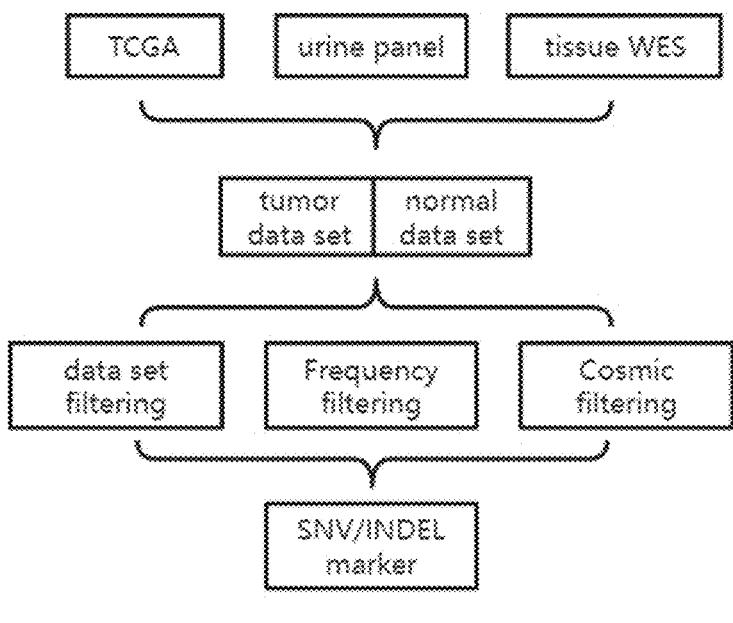

FIG. 3 illustrates a schematic structural diagram of determining multiple mutation markers of urothelial carcinoma according to an embodiment of the present application.

Figure 4:
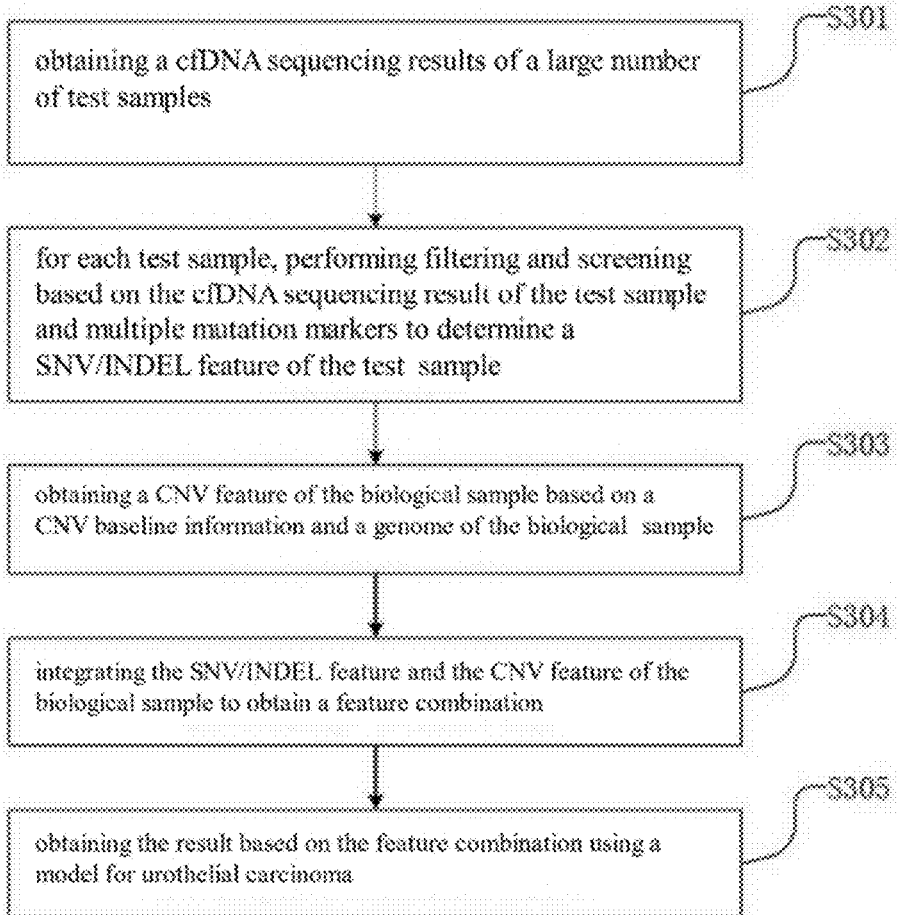

FIG. 4 illustrates a schematic flowchart of a method for constructing the urothelial carcinoma detection model according to an embodiment of the present application.

Figure 5:
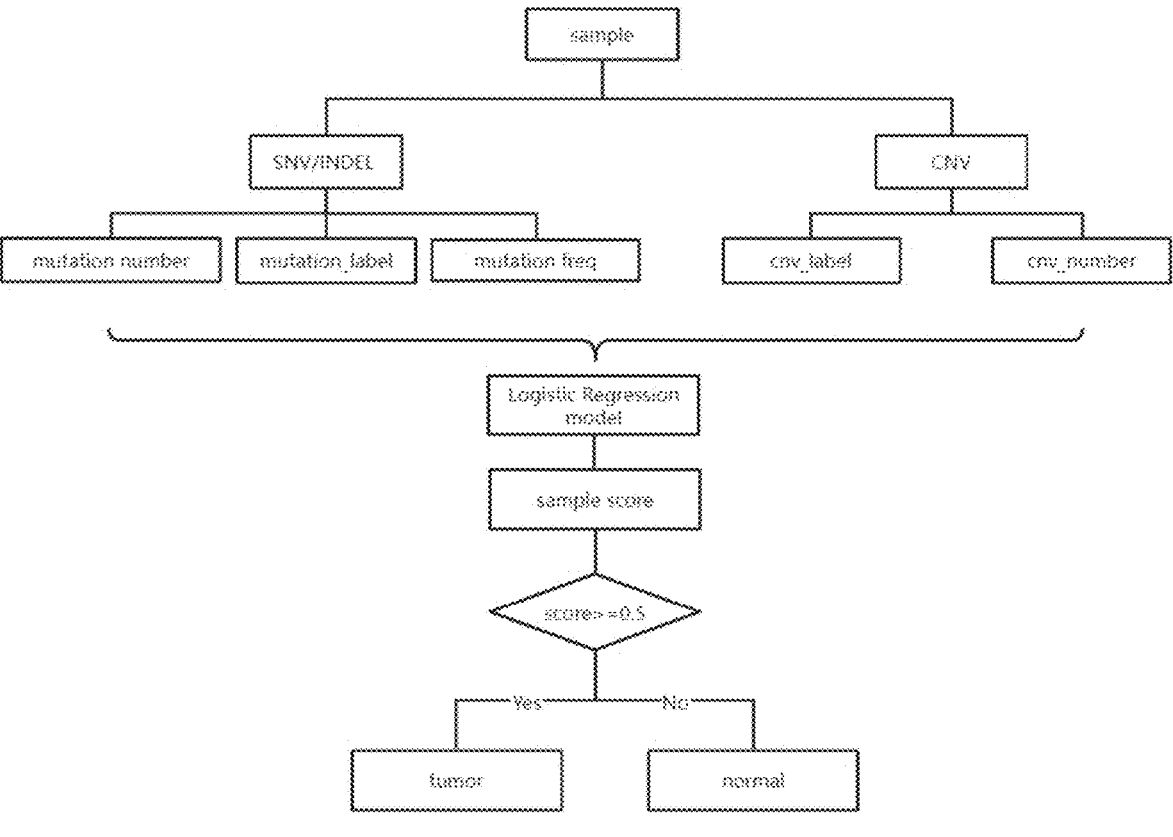

FIG. 5 illustrates an execution process of a test sample based on the urothelial carcinoma detection model according to an embodiment of the present application.

Figure 6:
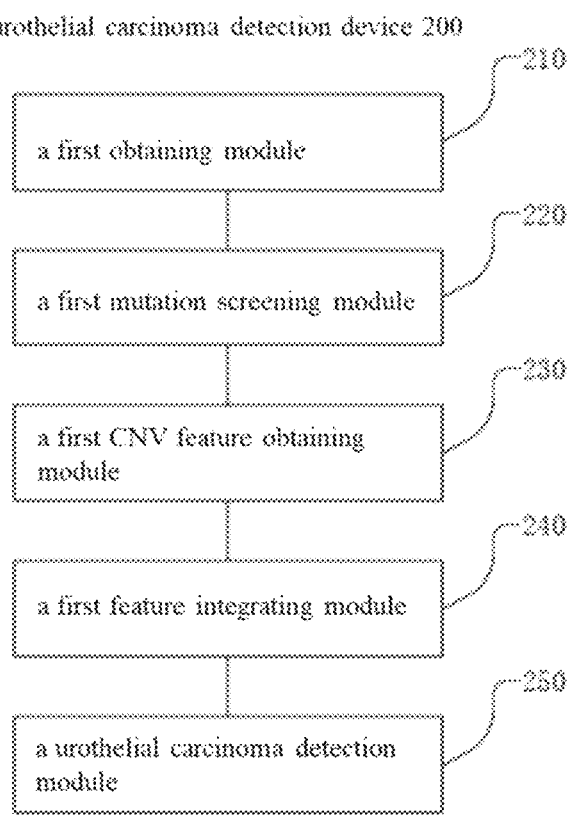

FIG. 6 illustrates a schematic structural diagram of a device for the urothelial carcinoma detection according to an embodiment of the present application.

Figures 7, 8:
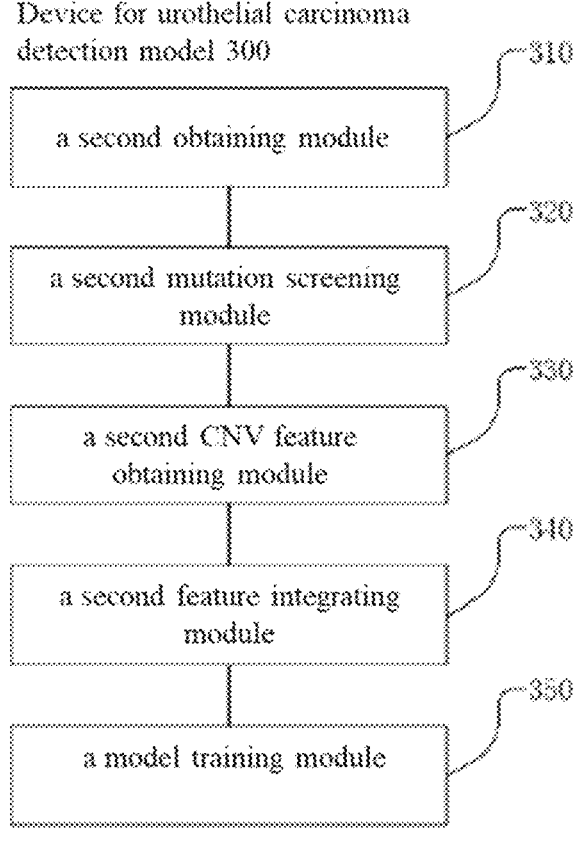

FIG. 7 illustrates a schematic structural diagram of a device for constructing a urothelial carcinoma detection model according to an embodiment of the present application.

FIG. 8 illustrates a schematic structural diagram of an electronic device according to an embodiment of the present application.

DETAILED DESCRIPTION

The present application will be further described in detail below with reference to FIGS. 1-8.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

For clear description of the objectives, technical solutions, and advantages of embodiments of the present disclosure, the technical solutions in the embodiments of the present disclosure will be described clearly and completely below with reference to the accompanying drawings in the embodiments of the present disclosure. It is apparent that the described embodiments are some of, not all the embodiments of the present disclosure. All other embodiments obtained by a person of ordinary skill in the art based on the embodiments of the present application without creative efforts shall fall within the protection scope of the present invention.

The term "and/or", as used herein, is only an association relationship for describing associated objects, indicating that there may be three kinds of relationships. For example, A and/or B may indicate three cases: A exists alone; A and B exist simultaneously; and B exists alone. In addition, the character "/" used herein generally indicates that the associated objects are in an "or" relationship.

The embodiments of the present application will be further described in detail below with reference to the accompanying drawings.

Nowadays, detection methods for urothelial carcinoma mainly include imaging techniques (CT, MRI, urography, B-ultrasound, etc.), cystoscopy combined with urine exfoliated cytology and FISH detection. However, the detection rate of ureteral tumors by imaging examinations such as CT and MRI is very low, and the positive rate of urine exfoliated cytology testing is less than 50%. Urine FISH testing is also limited by specimen conditions and tumor obstruction levels. Testing by ureteroscopy/flexible endoscopy is an invasive procedure and may increase the risk of bladder metastasis.

Therefore, in order to solve the above problems, the present application provides a method, a system, a device, or an equipment for detection of urothelial carcinoma, specifically for urothelial carcinoma at an early stage, which is a non-invasive detection with high testing performance, by using a urothelial carcinoma detection model.

In some embodiment, the method comprises Step S101: obtaining a cfDNA sequencing result of a biological sample.

In some embodiment, the biological sample is a urine sample. For example, the biological sample is from a subject with a tumor, a subject suspected to have a tumor, a subject with risk for tumor or a healthy subject. In some embodiment, the subject may be a subject who have not been treated with anti-cancer therapy and/or a subject who have been treated with anti-cancer therapy. A cfDNA sequencing information, genome information, a tumor cell content or other information may be obtained from the biological sample.

The cfDNA sequencing information of the biological sample may be obtained by using a kit. The cfDNA (cell free DNA) refers to partially degraded endogenous DNA that is free outside cells and mainly comes from cell apoptosis or necrosis. Since the half-life of cfDNA is very short (16 min), there is great potential to use cfDNA as a biomarker. In certain circumstances (e.g., cancer patients, pregnant women, patients undergoing organ transplantation, etc.), a small amount of cfDNA derived from "heterologous" cells (such as tumor cells, fetal cells, or donor cells) can be used as a marker for genetic testing.

In some embodiment, the method comprises Step S102: conducting filtering and screening based on the sequencing result of cfDNA of the biological sample and a mutation marker to determine a SNV/INDEL feature of the biological sample.

In some embodiment, the mutation marker is a marker that can distinguish a subject without urothelial carcinoma from a subject with urothelial carcinoma, and the SNV/INDEL feature includes: a mutation number, a mutation label, and a maximum mutation frequency.

In some embodiments, the method comprising matching the cfDNA sequencing information with more than one mutation markers one by one. If a mutation marker is detected in the cfDNA by sequencing, it is determined that the biological sample has a mutation, and the mutation number is counted. The mutation number refers to the number of mutation markers in the biological sample obtained by filtering and screening based on the cfDNA sequencing result of the biological sample and the mutation markers. The mutation label is used for characterizing whether the biological sample has a mutation corresponding to urothelial carcinoma, and the mutation label is determined by the mutation number. For example, if the number of mutations is 0, the mutation label is denoted 0; if the number of mutations is not 0, the mutation label is denoted 1. The corresponding relationship between the mutation label and the mutation number can be set by the skilled person in the art according to the actual situation, and it will not be limited in the embodiments of the present application. The maximum mutation frequency refers to the one with the highest mutation frequency among the corresponding mutation markers in the biological sample.

Further, the more than one mutation markers may be comprehensively determined by the mutation site filtering and screening based on public tumor data, internal samples and sequencing data sets. In some embodiments, the method for determining the mutation markers includes: filtering and screening sites in a large number of data sets in terms of population frequency, frequency in the Cosmic database, mutation frequency, mutation reads, mutations caused by oxidative damage, etc., wherein the large number of data sets may include: public tumor data, internal samples and sequencing data sets. The frequency generally refers to the number of samples with mutation.

The mutation markers capable of distinguishing a subject without urothelial carcinoma from a subject with urothelial carcinoma may comprises a mutation of FGFR3, a mutation of TERT, and/or a mutation of ERBB2.

As used herein, the term "TERT" generally refers to the gene encoding telomerase reverse transcriptase, also known as CMM9, DKCA2, DKCB4, EST2, PFBMFT1, TCS1, TP2, TRT, hEST2 or hTRT. The position of human TERT is in Chromosome 5: 1,253,262-1,295,184 reverse strand (GRCh37:CM000667.1). More information about the human TERT gene can be found under ensemble number ENSG00000164362. The mutations of the TERT gene in the present application can be expressed in one or more ways. For example, the two common promoter mutations of the TERT gene in the application are located 124 bp and 146 bp upstream of the ATG start site, including chr5:1295228 C>T (called C228T, also known in the art as c.-124C>T) and chr5:1295250 C>T (called C250T, also known in the art as c.-146C>T).

As used herein, the term "FGFR3" generally refers to the gene encoding fibroblast growth factor receptor 3, also known as ACH, CD333, CEK2, HSFGFR3EX or JTK4. The position of human FGFR3 is in Chromosome 4: 1,795,034-1,810,599 forward strand (GRCh37:CM000666.1). More information about the human FGFR3 gene can be found under ensemble number ENSG00000068078. The mutations involving the FGFR3 gene in the present application can be expressed in one or more ways. For example, the FGFR3 R248C mutation in the application can also be called chr4: 1803564 C>T in the art. (GRCh37), or "NM_000142 (FGFR3): c.742C>T (p.R248C)". For example, the FGFR3 S249C mutation in the application is also called chr4: 1803568 C>G in the art (GRCh37), or NM_000142 (FGFR3): c.746C>G (p.S249C)". For example, the FGFR3 Y373C mutation in the application is also called chr4: 1806099 A>G in the art (GRCh37), or NM_000142 (FGFR3): c.1118A>G (p.Y373C).

As used herein, the term "ERBB2" generally refers to the gene encodes Erb-B2 Receptor Tyrosine Kinase 2, which is a member of the epidermal growth factor (EGF) receptor family of receptor tyrosine kinases. More information about the human ERBB2 gene can be found under ensemble number ENSG00000141736. The mutations involving the ERBB2 gene in the present application can be expressed in one or more ways. For example, the ERBB2 mutation in the application can also be called c.929C>T, NM_000142 (ERBB2): c.929C>T (p.S310F) chr17: 37868208 A>G (GRCh37).

For example, the mutation marker of the method is selected from the group consisting of: TERT chr5: 1295228-1295228, TERT chr5: 1295250-1295250, FGFR3 chr4: 1803564-1803564, FGFR3 chr4: 1803568-1803568, FGFR3 chr4: 1807890-1807890, FGFR3 chr4: 1807889-1807889, FGFR3 chr4: 1806099-1806099, FGFR3 chr4: 1806092-1806092, FGFR3 chr4: 1806089-1806089, FGFR3 chr4: 1808937-1808937, ERBB2 chr17: 37868208-37868208, and FGFR3 chr4: 1806099-1806099.

For example, the mutation marker of the method is selected from the group consisting of: TERT chr5: 1295228-

1295228, TERT chr5: 1295250-1295250, FGFR3 chr4: 1803564-1803564, FGFR3 chr4: 1803568-1803568, FGFR3 chr4: 1807890-1807890, FGFR3 chr4: 1807889-1807889, FGFR3 chr4: 1806099-1806099, FGFR3 chr4: 1806092-1806092, FGFR3 chr4: 1806089-1806089, and FGFR3 chr4: 1808937-1808937.

For example, the mutation marker of the method is selected from the group consisting of: TERT chr5: 1295228-1295228, FGFR3 chr4: 1803564-1803564, TERT chr5: 1295250-1295250, FGFR3 chr4: 1803568-1803568, ERBB2 chr17: 37868208-37868208, and/or FGFR3 chr4: 1806099-1806099.

For example, the mutation marker of the method comprises TERT chr5: 1295228-1295228, FGFR3 chr4: 1803564-1803564, TERT chr5: 1295250-1295250, FGFR3 chr4: 1803568-1803568, ERBB2 chr17: 37868208-37868208, and/or FGFR3 chr4: 1806099-1806099. For example, the mutation marker of the method comprises TERT c.-124G>A, FGFR3 c.742C>T, TERT c.-146G>A, FGFR3 c.746C>G, ERBB2 c.929C>T, and/or FGFR3 c.1118A>G.

In some embodiment, the method comprises Step S103: obtaining a CNV feature of the biological sample based on a CNV baseline information and a genome of the biological sample. Optionally the CNV baseline is obtained from more than one samples from the healthy, wherein the CNV baseline information is obtained by computation based on multiple sample from healthy, the CNV baseline information includes: the expected read coverage and standard deviation of each bin, and the CNV feature includes: CNV number and CNV label.

In some embodiments, the CNV feature obtaining is performed on the basis of the CNV baseline information and the genome of the biological sample to obtain the CNV feature of the biological sample, wherein the CNV refers to copy number variation, and the CNV feature can be used as a basis for screening in early screening of urothelial carcinoma. During the operation of obtaining the CNV feature, it can be determined, based on different feature extraction standards, whether CNV occurs in the biological sample and the CNV number. The feature extraction standards include but are not limited to: a CNV score of a chromosome in the genome of the biological sample, and the ratio of the length of the segment where CNV occurs to the length of the chromosome. The CNV feature includes a CNV number and/or a CNV label. The CNV number refers to the total number of CNVs appearing in the genome of the biological sample. The CNV label is determined by the CNV number. For example, if the CNV number is 0, the CNV label will be denoted 0; if the CNV number is not 0, the CNV label is denoted 1. The corresponding relationship between the CNV label and the CNV number can be set by the skilled person in the art according to the actual situation, and it will not be limited in the embodiments of the present application.

In some embodiments, the CNV baseline information is obtained by computation based on the genome of more than one healthy-person. For example, the genome of each sample from healthy may be divided into bins by a 1M window, and the read coverage of each bin is calculated. Then, the read coverage of the bins in the genome of all sample from healthy is processed to obtain the CNV baseline information. The CNV baseline information includes: an expected read coverage and a standard deviation of each bin, wherein the expected read coverage of each bin is based on the average of the read coverage of each bin in the genome of all sample from healthy, and the standard deviation is also obtained by performing variance processing based on all sample from healthy.

In order to improve the accuracy of the CNV feature of the biological sample, obtaining the CNV feature of the biological sample based one the CNV baseline information and the genome of the biological sample includes:

1) obtaining segment CNV scores of more than one segment corresponding to the genome of the biological sample based on the CNV baseline information and the genome of the biological sample;

2) determining a chromosomal CNV score of each chromosome in the biological sample based on the segment CNV score of the segment of the biological sample;

3) for the chromosomal CNV score of each chromosome in the biological sample, determining whether the absolute value of the chromosomal CNV score is greater than a first threshold; if so, determining a CNV mark of the chromosome as a positive mark; if not, determining the CNV mark corresponding to the chromosome as a negative mark;

4) obtaining a first CNV number of the biological sample based on the CNV mark of all chromosomes; and 5) determining a CNV feature based on the first CNV number.

In some embodiments, based on the CNV baseline information and the genome of the biological sample, the CNV score of each bin in the genome of the biological sample is determined, wherein the CNV score is for reflecting the difference between each bin in the biological sample and the corresponding bin in the CNV baseline information. Then, based on the corresponding CNV scores of all bins in the genome of the biological sample, the intervals are merged to obtain the segment CNV scores of more than one segments of the genome of the biological sample. Preferably, according to the CBS method, some bins that are consecutive and have close CNV scores are connected into a segment, and for each segment, based on the corresponding CNV scores of all bins corresponding to the segment, the segment CNV score corresponding to the segment is calculated.

In some embodiments, the first CNV number of the biological sample is determined based on a chromosomal CNV score of the corresponding chromosome. The biological sample includes 24 chromosomes, and each chromosome comprises a plurality of segments. Therefore, for each chromosome, the corresponding CNV scores of all segments in the chromosome are averaged to obtain the chromosomal CNV score corresponding to each chromosome, and the CNV scores of the 24 chromosomes corresponding to the biological sample can be obtained.

The method may comprise, for the chromosomal CNV score of each chromosome, determining whether the absolute value of the chromosomal CNV score is greater than the first threshold. If so, the CNV mark of the chromosome is determined as a positive mark. If not, the CNV mark corresponding to the chromosome is determined as a negative mark. The first threshold herein is obtained on the basis of a large amount of experimental data. The first threshold may be set by the skilled person in the art according to the actual situation. Preferably, the first threshold is set to be 5.5. Based on the CNV marks of the 24 chromosomes in the biological sample, the CNV mark determined as a positive mark is denoted 1, and the CNV mark determined as a negative mark is denoted 0. Then, the values represented by all CNV marks are added up, and the final addition result is denoted the first CNV number corresponding to the biological sample. Then, if the first CNV number is 0, the CNV label is denoted 0; if the CNV number is not 0, the CNV label is denoted 1. The CNV feature can be determined on the basis of the first CNV number and the CNV label.

In some embodiments, based on the CNV baseline information and the genome of the biological sample, the segment CNV scores of multiple segments of the genome of the biological sample are determined; then, based on the segment CNV scores of all segments of the biological sample, the chromosomal CNV score of each corresponding chromosome in the biological sample is determined, and based on the chromosomal CNV scores, the first CNV number of the biological sample is determined, and based on the first CNV number, the CNV feature is determined. The first CNV number of the biological sample is determined according to the chromosomal CNV score in the genome of the biological sample, and then the CNV feature is determined, which improves the accuracy of the CNV feature corresponding to the biological sample.

In some embodiments, in order to improve the accuracy of the CNV feature corresponding to the biological sample, subsequent to the operation of based on the CNV baseline information and the genome of the biological sample, obtaining segment CNV scores of multiple segments corresponding to the genome of the biological sample, further includes:

providing a tumor cell content of the biological sample, and 1-2) based on a relationship between the tumor cell content in the biological sample and a second threshold, determining a second CNV number of the biological sample;

for each segment of each chromosome in the biological sample, if the absolute value of the segment CNV score of the segment is greater than a third threshold, denoting the segment as a CNV interval;

for each chromosome in the biological sample, determining a feature ratio according to all CNV intervals of the chromosome, wherein the feature ratio refers to the ratio of the length of all CNV intervals of the chromosome to the length of the chromosome;

or each chromosome in the biological sample, determining whether the feature ratio is greater than a fourth threshold; if so, determining the CNV mark of the chromosome as a positive mark; if not, determining the CNV mark of the chromosome as a negative mark; and based on the CNV markers of all chromosomes, obtaining a third CNV number of the biological sample.

In some embodiments, since the tumor cell content can reflect the severity of a tumor, the tumor cell content of the biological sample is obtained, and in terms of the tumor cell content of the biological sample, the second CNV number corresponding to the biological sample is determined, and it is determined whether the tumor cell content in the biological sample is greater than the second threshold. If so, the second CNV number corresponding to the biological sample is denoted 1. If not, the second CNV number corresponding to the biological sample is denoted 0. The second threshold herein is obtained on the basis of a large amount of experimental data. The second threshold can be set by the skilled person in the art according to the actual situation.

For all segments of each chromosome in the biological sample, the absolute value of the CNV score of each segment can be compared with the third threshold. If the absolute value is greater than the third threshold, the corresponding segment is denoted a CNV interval. The third threshold herein is obtained on the basis of a large amount of experimental data. The third threshold can be set by the skilled person in the art according to the actual situation.

Preferably, the third threshold is 5. Then, for each chromosome in the biological sample, all CNV intervals of the chromosome are added up, and the ratio of the summed length of all CNV intervals to the length of the chromosome is calculated, and this ratio is used as the feature ratio of the chromosome, and, for the 24 chromosomes in the biological sample, the corresponding 24 feature ratios will be obtained.

In some embodiments, the method further comprises: based on the feature ratio of each chromosome, comparing the feature ratio with a fourth threshold. If the feature ratio is greater than the fourth threshold, the CNV mark of the chromosome is determined as a positive mark. If the feature ratio is not greater than the fourth threshold, the CNV mark of the chromosome is determined as a negative mark. The fourth threshold herein is obtained on the basis of a large amount of experimental data. The fourth threshold can be set by the skilled in the art according to the actual situation. Preferably, the fourth threshold is 0.3. Based on the corresponding CNV marks of the 24 chromosomes in the biological sample, the CNV mark determined as a positive mark is denoted 1, and the CNV mark determined as a negative mark is denoted 0. Then, the values represented by all CNV marks are added up, and the final addition result is denoted the third CNV number of the biological sample.

Accordingly, determining the CNV feature based on the first CNV number includes: based on the first CNV number and the target CNV number, comprehensively determining the CNV number, wherein the target CNV number is any one or more of the second CNV number and the third CNV number; and based on the CNV number, determining the CNV feature.

In some embodiments, in the operation of determining the CNV feature on the basis of the CNV number, the CNV number can be comprehensively determined on the basis of the first CNV number and the target CNV number, and then the CNV feature can be determined on the basis of the CNV number. The operation of determining the CNV number may be implemented in many ways: determining the CNV number on the basis of the first CNV number and the second CNV number, determining the CNV number on the basis of the first CNV number and the third CNV number, and determining the CNV number on the basis of the first CNV number, the second CNV number and the third CNV number. The CNV number is comprehensively determined in terms of multiple dimensions, thereby improving the accuracy of the CNV feature corresponding to the biological sample.

In some embodiments, the second CNV number of the biological sample is determined on the basis of the tumor cell content in the biological sample; the CNV interval is determined on the basis of the segment CNV scores, and then the feature ratio is determined on the basis of all CNV intervals corresponding to the chromosome, and then the third CNV number of the biological sample is determined on the basis of the feature ratio; then, the CNV number and the CNV feature are comprehensively determined on the basis of the first CNV number, the second CNV number and the third CNV number. The CNV number of the biological sample may be comprehensively determined through the combination of the three dimensions of chromosomal CNV score, tumor cell content, and feature ratio, thereby further improving the accuracy of the CNV feature of the biological sample.

In some embodiments, in order to more conveniently determine the CNV interval on the basis of the segment CNV score. In some embodiments, obtaining segment CNV scores of multiple segments of the genome of the biological sample based on the CNV baseline information and the genome of the biological sample includes: based on the CNV baseline information and the genome of the biological sample, determining the CNV score of each bin in the genome of the biological sample, wherein the CNV score is for reflecting the difference between each bin in the biological sample and the corresponding bin in the CNV baseline information; and based on the CNV scores of all bins in the genome of the biological sample, merging the intervals to obtain the segment CNV scores of multiple segments corresponding to the genome of the biological sample, wherein the segment is obtained by merging consecutive bins.

In some embodiments, the CNV baseline information includes: the expected read coverage and standard deviation of each bin. Preferably, the read coverage of each bin used during the operation of determining the CNV baseline information is GC corrected and self-standardized. Based on the CNV baseline information and the biological sample, the process of determining the CNV score of each bin in the biological sample is specifically: calculating the ratio of the bin according to the formula: ratio=RCbin (the biological sample)/RCbin (baseline), where RCbin (the biological sample) represents the read coverage of the bin of the biological sample, and RCbin (baseline) represents the expected read coverage of the bin in the CNV baseline information. Then, based on the ratio and CNV baseline information of each bin, determining the CNV score of each bin. Specifically, the calculation is performed according to the CNV score formula: Z-Score=(ratio−E(ref-ratio))/std (ref-ratio), where ratio represents the ratio of the corresponding bin, E(ref-ratio) represents the average ratio of the corresponding bin in the CNV baseline information, and std(ref-ratio) represents the standard deviation of the corresponding bin in the CNV baseline information. Therefore, the CNV score can be for reflecting the difference between each bin in the biological sample and the corresponding bin in the CNV baseline information.

In some embodiments, the method comprises, based on the CNV scores of all bins in the genome of the biological sample, merging the intervals to obtain the segment CNV scores of multiple segments of the genome of the biological sample. Preferably, the segment CNV scores of multiple segments of the genome of the biological sample are obtained by using a CBS method. Specifically, according to the CBS method, some bins that are consecutive and have close CNV scores can be connected into a segment, and for each segment, based on the corresponding CNV scores of all bins corresponding to the segment, the segment CNV score of the corresponding segment is calculated. Therefore, by using the CBS method, multiple segments corresponding to the genome of the biological sample and the segment CNV scores of all the segments can be obtained.

In some embodiments, based on the CNV baseline information and the genome of the biological sample, the CNV score of each bin in the genome of the biological sample is determined, and based on the corresponding CNV scores of all the bins in the genome of the biological sample, the intervals are merged to obtain the segment CNV scores of multiple segments of the genome of the biological sample, and then, the CNV interval can be more conveniently determined according to the segment CNV score to determine the CNV feature.

In some embodiments, in order to make the CNV baseline information more accurately adapted to the situation of healthy people, the operation of determining the CNV baseline information includes:

obtaining the genomes of multiple sample from healthy; for each sample from healthy, calculating the CNV sliding window coverage on the basis of the genome of the sample from healthy to obtain the read coverage of each bin in the genome of the sample from healthy; determining the CNV baseline information on the basis of the read coverage of each of bins of the genomes of all the sample from healthy, wherein the CNV baseline information includes: the expected read coverage and standard deviation of each bin.

In some embodiments, the CNV baseline information is obtained by the processing of multiple sample from healthy. In this way, the CNV baseline information can be more accurately adapted to the situation of healthy people. For each sample from healthy, CNV sliding window coverage calculation is performed on the sample from the healthy to obtain the read coverage of each bin in the sample from healthy. The specific operation of calculating the CNV sliding window coverage includes: dividing the genome of each sample from healthy into bins by a 1M window, and calculating the read coverage of each bin. The read coverage of the bin is determined by adding up reads having a start position or end position located in the bin, wherein the sum of the reads is denoted RC, and the value of RC is the read coverage of the bin. For each bin in each sample from healthy, after the read coverage corresponding to each bin is obtained, it is preferred to perform GC correction on all read coverages and then perform self-standardization. GC correction is performed to obtain a more accurate read coverage, and the self-standardization is performed to eliminate the impact of differences in data volume of sample from healthy on the read coverage. Since the read coverage of each bin determined according to the genomes of different sample from healthy is different, corresponding processing needs to be performed on the basis of multiple samples from healthy to make the read coverage of each bin more accurate.

In some embodiments, after the calculation of the CNV sliding window coverages of the genomes of all the sample from healthy is completed, the CNV baseline information is determined on the basis of the read coverage of each bin of the genomes of all the sample from healthy, wherein the CNV baseline information includes: the expected read coverage and standard deviation. Specifically, the read coverage of each bin in the genome of all healthy human samples is processed accordingly to obtain the CNV baseline information. Briefly, the read coverage of a bin in the CNV baseline information is processed on the basis of the read coverage of the bin in the genomes of all the sample from healthy. For example, if 90 sample from healthy are selected to determine CNV baseline information, the operation will be based on the read coverages of all bins in the genomes of the 90 sample from healthy. The final CNV baseline information obtained includes: the expected read coverage and standard deviation of each bin. For a bin, the expected read coverage of the bin is based on the average of 90 read coverages, corresponding to the bin, in the genomes of 90 sample from healthy. The read standard deviation of the bin is also based on the standard deviation of the 90 read coverages corresponding to the bin in the genomes of 90 sample from healthy.

In some embodiments, the CNV sliding window coverage is calculated on the basis of the genome of each sample from healthy to obtain the read coverage of each bin in the genome of each sample from healthy, and the CNV baseline information is then determined on the basis of the read coverage of each bin corresponding to the genomes of all the sample from healthy. In this way, the CNV baseline information can be more accurately adapted to the situation of healthy people.

In some embodiments, to make the read coverage of the bin more accurate, calculating the CNV sliding window coverage on the basis of the genome of the sample from healthy to obtain the read coverage of each bin in the genome of the sample from healthy includes: for each sample from healthy, dividing the genome of the sample from healthy into multiple bins; for each bin, adding up reads having a start position or end position located in the bin to obtain an initial read coverage corresponding to each bin; and for each bin, performing GC correction and self-standardization on the basis of the initial read coverage to obtain the read coverage of each bin in the genome of the sample from healthy.

In the embodiments, for each sample from healthy which includes 24 chromosomes, and bins are divided on the basis of each chromosome to obtain all bins of the sample from healthy. Preferably, the bins are divided by a 1M window. For each bin, by adding up the reads having a start position or end position located in the bin, the initial read coverage corresponding to each bin is obtained, wherein the read is an interval, including a start position and an end position. In some embodiments, if the start position or end position of the read is located in the bin, then the number of reads in the bin is added by 1, and the sum of reads in the bin is considered as the corresponding initial read coverage. For a clearer description, the initial read coverage corresponding to each bin is obtained by adding up the reads having a start position or end position located in the bin. As shown in FIG. 2, in a bin, the sum of reads having a start position or end position located in the bin is 4.

In some embodiments, for each bin, after the initial read coverage corresponding to the bin is obtained, GC correction and self-standardization are performed to make the read coverage of the bin more accurate, and the processed read coverage of each bin is denoted the read coverage of each bin in the sample from healthy. Specifically, the operation of performing GC correction on the initial read coverage (RC) may include: calculating a correction coefficient by loess regression and then obtaining the GC-corrected read coverage (RCgc) according to the formula: $RCgc=RC*correction$ coefficient. Then, the GC-corrected read coverage is self-standardized. The operation of self-standardization is calculation according to the self-standardization formula $RCbin=RCgc\text{-}bin/mean\ (RCgc\text{-}all\text{-}bin)$, where RCgc-bin represents the GC-corrected read coverage of each bin, and mean (RCgc-all-bin) represents the mean of the GC-corrected read coverages of all bins in this sample from healthy. Therefore, by performing GC correction and self-normalization on the initial read coverage, Rcbin is considered as the read coverage of each bin in the genome of the sample from healthy.

In some embodiments, for each sample from healthy, the genome of the sample from healthy may be divided into multiple bins, and based on the sum of reads having a start position or end position located in the bin, the initial read coverage of each bin is obtained, and then GC correction and self-normalization are performed on the basis of the initial read coverage to obtain the read coverage of each bin in the genome of the sample from healthy. Performing GC correction and self-normalization on the initial read coverage can make the read coverage of the bin more accurate.

In some embodiment, the method comprises Step S104: integrating the SNV/INDEL feature and the CNV feature of the biological sample to obtain a feature combination. In some embodiments, integrating the SNV/INDEL feature and the CNV feature of the biological sample comprising integrating the mutation number, the mutation label, and the maximum mutation frequency in the SNV/INDEL feature with the CNV number and the CNV label in the CNV feature of the biological sample to obtain the feature combination of the biological sample, wherein the feature combination can be in the form of a feature matrix.

In some embodiment, the method comprises Step S105: obtaining the result based on the feature combination using a model for urothelial carcinoma. In some embodiments, the model for urothelial carcinoma is obtained by training more than one training examples, wherein the urothelial carcinoma early screening model is trained using more than one test samples.

In some embodiment, the feature combination is sent to s urothelial carcinoma detection model to perform urothelial carcinoma screening and obtain the screening result, the status of the biological sample can be quickly and accurately obtained through the screening result, wherein the screening result include positive and negative.

In some embodiment, a logistic regression model is trained on the basis of a large number of training sets, validation sets and test sets to obtain the urothelial carcinoma detection model, wherein the training sets, the validation sets and the test sets include a large number of samples from healthy subject and samples from a subject with a tumor. And when the logistic regression model is trained using the test sets, only if both the sensitivity and specificity in the test result exceed their corresponding thresholds, it indicates that the logistic regression model is successfully trained, and the successfully trained logistic regression model is regarded as a urothelial carcinoma detection model.

In some embodiments, the SNV/INDEL feature of a biological sample is determined based on the cfDNA sequencing result of the biological sample and the mutation markers; a CNV feature of a biological sample is determined based on the CNV baseline information and the genome of the biological sample, and then the SNV/INDEL feature and the CNV feature of the biological sample are integrated to obtain a feature combination. Then the urothelial carcinoma detection model is used for urothelial carcinoma screening to obtain a screening result based on the feature combination. The accuracy of the method for urothelial carcinoma detection, particularly for detecting urothelial carcinoma at an early stage, is higher than the known method.

In some embodiments, in order to enable the mutation markers to accurately distinguish healthy people from patients with urothelial carcinoma, the operation for determining a mutation marker may include: performing mutation site filtering and screening on the basis of public tumor data, internal samples and sequencing data sets.

For the embodiment of this application, the public tumor data is data obtained from a TCGA database, wherein the TCGA database, as the preferred public database for cancer research, integrates multi-omics data of various cancers, mainly including DNA, mRNA, miRNA, total RNA sequencing, methylation, copy number and other data types. The internal samples are processed urine samples from internal urothelial carcinoma patients. At least the cfDNA sequencing result, genome, tumor cell content, etc. corresponding to the internal urine samples can be obtained. Of course, more other information may also be obtained and it will not be limited in the embodiments of the present application. The sequencing data set may be whole-exome sequencing of internal urothelial carcinoma patients, based on the whole-exome method. The whole-exome testing is a method that detects all exons of all human genes and is suitable for the diagnosis of some complex genetic diseases that are difficult to determine. In clinical practice, whole-exome testing will be chosen for those that are suspected to have genetic factors and of which clinical phenotypes are genetically heterogeneous. Although exons only account for 1%-2% of the human genome, they contain 85% of pathogenic variants, so WES is a relatively simple and rapid diagnostic solution.

Further, mutation filtering and screening may be performed on the basis of public tumor data, internal samples and sequencing data sets, and all sites were filtered and screened in terms of population frequency, frequency in the Cosmic database, mutation frequency, mutation reads, mutations caused by oxidative damage, etc., and 148 mutation markers that can distinguish sample from healthy from samples from patients with urothelial carcinoma are finally screened, as shown in FIG. 3. In FIG. 3, the tumor data set represents a sample from a patient with urothelial carcinoma, the normal data set represents a sample from healthy, data set filtering represents the data set filtering of sites, Frequency filtering represents the mutation frequency of the population frequency filtering site, and Cosmic filtering represents filtering the frequency of occurrence of sites in the Cosmic database. The population frequency comes from the public database, and the population frequency in the public database is obtained by statistics of a large amount of data.

In some embodiments, the mutation site filtering and screening is performed on the basis of public tumor data, internal samples and sequencing data sets to determine multiple mutation markers corresponding to urothelial carcinoma, such that mutation markers can accurately distinguish healthy people from patients with urothelial carcinoma.

On other aspects, the present application provides a method for constructing a urothelial carcinoma detection model, executed by an electronic device, as shown in FIG. 4. The method includes step S301, step S302, step S303, step S304 and/or step S305, wherein, Step S301: obtaining a cfDNA sequencing results of a large number of test samples, wherein the large number of test samples include a number of samples from healthy people and a number of samples from patients with urothelial carcinoma.

In some embodiments, the cfDNA sequencing results of a large number of test samples are obtained, wherein the large number of test samples include a number of control samples and a number of samples from subjects with urothelial carcinoma. There will be a type label for each test sample, and the type label is used to distinguish samples from healthy people and samples from patients with urothelial carcinoma.

Step S302: for each test sample, performing filtering and screening based on the cfDNA sequencing result of the test sample and multiple mutation markers to determine a SNV/INDEL feature of the test sample, wherein the mutation markers are markers that can distinguish normal people from patients with urothelial carcinoma, and the SNV/INDEL feature includes: mutation number, mutation label, and maximum mutation frequency.

In the embodiments, for each test sample, the process of performing filtering and screening based on the cfDNA sequencing result and multiple mutation markers to determine the SNV/INDEL feature of the test sample is the same as the corresponding processing on the biological sample in step S102. That is, the process of processing the biological sample is also applicable to the test sample, so it will not be stated again in the embodiments of the present application. After the operation of determining the SNV/INDEL feature of each test sample, the corresponding SNV/INDEL features of all the test samples are obtained.

Step S303: obtaining a CNV feature of the biological sample based on a CNV baseline information and a genome of the biological sample. Optionally the CNV baseline is obtained from more than one samples from the healthy, wherein the CNV baseline information is obtained by computation based on multiple samples from healthy, the CNV baseline information includes: the expected read coverage and standard deviation of each bin, and the CNV feature includes: CNV number and CNV label.

Step S304: integrating the SNV/INDEL feature and the CNV feature of the biological sample to obtain a feature combination. In some embodiments, integrating the SNV/INDEL feature and the CNV feature of the biological sample comprising integrating the mutation number, the mutation label, and the maximum mutation frequency in the SNV/INDEL feature with the CNV number and the CNV label in the CNV feature of the biological sample to obtain the feature combination of the biological sample, wherein the feature combination can be in the form of a feature matrix.

Step S305: obtaining the result based on the feature combination using a model for urothelial carcinoma. In some embodiments, the model for urothelial carcinoma is obtained by training more than one training examples, wherein the urothelial carcinoma early screening model is trained using more than one test samples.

In some embodiments, the model training is performed on the basis of all feature combinations corresponding to a large number of test samples to obtain a urothelial carcinoma detection model. Specifically, all feature combinations corresponding to a large number of test samples are divided into training, validation and test sets, and the logistic regression model is trained on the basis of a large number of training, validation and test sets. The training, validation and test sets include a large number of normal samples and cancer samples. And when the logistic regression model is tested using the test sets, only if both the sensitivity and specificity in the test result exceed their corresponding thresholds, it indicates that the logistic regression model is successfully trained, and the successfully trained logistic regression model is regarded as a urothelial carcinoma detection model.

On other aspects, the present application provides a device for urothelial carcinoma detection device 200. As shown in FIG. 6, the urothelial carcinoma detection device 200 may specifically include:

a first obtaining module 210, configured to obtain a cfDNA sequencing result of a biological sample;

a first mutation screening module 220, configured to perform filtering and screening based on the cfDNA sequencing result and multiple mutation markers to determine a SNV/INDEL feature of the biological sample, wherein the mutation markers are markers that can distinguish healthy people from patients with urothelial carcinoma, and the SNV/INDEL feature includes: mutation number, mutation label, and maximum mutation frequency;

a first CNV feature obtaining module 230, configured to obtain CNV baseline information and the genome of the biological sample, and perform CNV feature obtaining based on the CNV baseline information and the genome of the biological sample to obtain a CNV feature of the biological sample, wherein the CNV baseline information is obtained in advance by computation based on multiple sample from healthy, the CNV baseline information includes: the expected read coverage and standard deviation of each bin, and the CNV feature includes: CNV number and CNV label.

a first feature integrating module 240, configured to integrate the SNV/INDEL feature and CNV feature corresponding to the biological sample to obtain a feature combination; and a urothelial carcinoma detection module 250, configured to based on the feature combination, perform urothelial carcinoma screening by using a urothelial carcinoma detection model to obtain a screening result, wherein the urothelial carcinoma detection model is trained using a large number of test samples.

In some embodiment, based on the cfDNA sequencing result of the biological sample and the multiple mutation markers, the filtering and screening is performed to determine a SNV/INDEL feature; based on the CNV baseline information and the genome of the biological sample, CNV feature obtaining is performed to obtain a CNV feature, and then the SNV/INDEL feature and CNV feature corresponding to the biological sample are integrated. Based on the feature combination, the urothelial carcinoma detection model is used for urothelial carcinoma screening to obtain a screening result. Use of the urothelial carcinoma detection model for cancer screening achieves non-invasive detection, and based on the SNV/INDEL feature and CNV feature corresponding to the biological sample, the accuracy of screening for urothelial carcinoma is higher.

In some embodiment, when executing the operation of performing CNV feature obtaining based on the CNV baseline information and the genome of the biological sample to obtain the CNV feature of the biological sample, the first CNV feature obtaining module is configured to:

based on the CNV baseline information and the genome of the biological sample, obtain segment CNV scores of multiple segments corresponding to the genome of the biological sample;

based on the corresponding segment CNV scores of all the segments of the biological sample, determining a chromosomal CNV score corresponding to each chromosome in the biological sample;

or the chromosomal CNV score corresponding to each chromosome in the biological sample, determine whether the absolute value of the chromosomal CNV score is greater than a first threshold; if so, determine a CNV mark corresponding to the chromosome as a positive mark; if not, determine the CNV mark corresponding to the chromosome as a negative mark;

based on the corresponding CNV marks of all chromosomes, obtain a first CNV number corresponding to the biological sample; and based on the first CNV number, determine a CNV feature.

In some embodiments, the urothelial carcinoma detection device 200 further includes:

a comprehensive CNV feature obtaining module, configured to: obtain the tumor cell content of the biological sample, and based on a relationship between the tumor cell content in the biological sample and a second threshold, determine a second CNV number corresponding to the biological sample;

for each segment of each chromosome in the biological sample, if the absolute value of the segment CNV score corresponding to the segment is greater than a third threshold, denote the segment as a CNV interval;

for each chromosome in the biological sample, determine a feature ratio according to all CNV intervals corresponding to the chromosome, wherein the feature ratio refers to the ratio of the length of all CNV intervals corresponding to the chromosome to the length of the chromosome;

for each chromosome in the biological sample, determine whether the feature ratio is greater than a fourth threshold; if so, determine the CNV mark corresponding to the chromosome as a positive mark; if not, determine the CNV mark corresponding to the chromosome as a negative mark; and based on the corresponding CNV markers of all chromosomes, obtain a third CNV number corresponding to the biological sample.

Accordingly, when executing the operation of based on the first CNV number, determining the CNV feature, the first CNV obtaining module 230 is configured to:

based on the first CNV number and the target CNV number, comprehensively determine the CNV number, wherein the target CNV number is any one or more of the second CNV number and the third CNV number; and based on the CNV number, determine the CNV feature.

In some embodiment, when executing the operation of obtaining segment CNV scores of multiple segments corresponding to the genome of the biological sample on the basis of the CNV baseline information and the genome of the biological sample, the first CNV feature obtaining module 230 is configured to:

based on the CNV baseline information and the genome of the biological sample, determine the CNV score of each bin in the genome of the biological sample, wherein the CNV score is for reflecting the difference between each bin in the biological sample and the corresponding bin in the CNV baseline information; and based on the corresponding CNV scores of all bins in the genome of the biological sample, merging the bins to obtain the segment CNV scores of multiple segments corresponding to the genome of the biological sample, wherein the segment is obtained by merging consecutive bins.

In some embodiment, the urothelial carcinoma detection device 200 further includes:

a CNV baseline information determining module, configured to obtain the genomes of multiple sample from healthy;

for each sample from healthy, calculate the CNV sliding window coverage on the basis of the genome of the sample from healthy to obtain the read coverage of each bin in the genome of the sample from healthy; and determine the CNV baseline information on the basis of the read coverage of each of bins corresponding to the genomes of all the sample from healthy, wherein the CNV baseline information includes: the expected read coverage and standard deviation of each bin; the expected read coverage is determined on the basis of the average of the read coverages of all sample from healthy in each bin, and the standard read deviation is determined by variance processing based on the read coverages of all the sample from healthy in each bin.

In some embodiment, when executing the operation of for each sample from healthy, calculating the CNV sliding window coverage on the basis of the genome of the sample from healthy to obtain the read coverage of each bin in the genome of the sample from healthy, the CNV baseline information determining module is configured to:

for each sample from healthy, divide the genome of the sample from healthy into multiple bins;

for each bin, add up reads having a start position or end position located in the bin to obtain an initial read coverage corresponding to each bin; and for each bin, perform GC correction and self-standardization on the basis of the initial read coverage to obtain the read coverage of each bin in the genome of the sample from healthy.

In some embodiment, the urothelial carcinoma detection device 200 further includes:

performing mutation site filtering and screening on the basis of public tumor data, internal samples and sequencing data sets to determine multiple mutation markers corresponding to urothelial carcinoma.

Those skilled in the art can clearly understand that for the convenience and simplicity of description, the specific working process of the urothelial carcinoma detection device 200 described above can be referred to the corresponding process in the foregoing method embodiment, and will not be repeated here.

The above embodiment introduces a method for constructing a urothelial carcinoma detection model from the perspective of method flow. The following embodiment introduces a device for constructing a urothelial carcinoma detection model from the perspective of virtual modules or virtual units. For details, see the following embodiment.

In another aspect, the present application provides a device for constructing a urothelial carcinoma detection model 300. As shown in FIG. 7, the device for constructing a urothelial carcinoma detection model 300 may specifically include:

a second obtaining module 310, configured to obtain corresponding cfDNA sequencing results of a large number of test samples, wherein the large number of test samples include a number of samples from healthy people and a number of samples from patients with urothelial carcinoma;

a second mutation screening module 320, configured to, for each test sample, perform filtering and screening based on the cfDNA sequencing result corresponding to the test sample and multiple mutation markers to determine a SNV/INDEL feature of the test sample, wherein the mutation markers are markers that can distinguish healthy people from patients with urothelial carcinoma, and the SNV/INDEL feature includes: mutation number, mutation label, and maximum mutation frequency;

a second CNV feature obtaining module 330, configured to for each test sample, perform CNV feature obtaining based on CNV baseline information and the genome of the test sample to obtain a CNV feature of the test sample, wherein the CNV feature includes: CNV number and CNV label;

a second feature integrating module 340, configured to for each test sample, integrate the SNV/INDEL feature and CNV feature corresponding to the test sample to obtain a feature combination; and a model training module 350, configured to perform model training based on all feature combinations corresponding to a large number of test samples to obtain a urothelial carcinoma detection model.

In some embodiment, the corresponding cfDNA sequencing results of a large number of test samples are obtained, where the large number of test samples include a number of samples from healthy and a number of samples from patients with urothelial carcinoma. For each test sample, the filtering and screening is performed on the basis of the cfDNA sequencing result of the test sample and multiple mutation markers to determine the SNV/INDEL feature; based on the CNV baseline information and the genome of the test sample, CNV feature obtaining is performed to obtain the CNV feature, and then the SNV/INDEL feature and CNV feature corresponding to the test sample are integrated to obtain a feature combination. Then, model training is performed on the basis of all feature combinations corresponding to a large number of test samples to obtain a urothelial carcinoma detection model. Training the model based on a large number of feature combinations can make the screening result more accurate during the screening based on the urothelial carcinoma detection model, that is, the sensitivity and specificity are both high.

Those skilled in the art can clearly understand that for the convenience and simplicity of description, the specific working process of the device 300 for constructing a urothelial carcinoma detection model described above can be referred to the corresponding process in the foregoing method embodiment, and will not be repeated here.

In another aspect, the present application provides an electronic device, as shown in FIG. 8. The electronic device 400 shown in FIG. 8 includes a processor 401 and a memory 403. The processor 401 and the memory 403 are connected, for example, by a bus 402. Optionally, the electronic device 400 may also include a transceiver 404. It should be noted that in practical applications, the number of transceivers 404 is not limited to one, and the structure of the electronic device does not constitute a limitation on the embodiments of the present application.

The processor 401 may be a CPU (Central Processing Unit), a general-purpose processor, a DSP (Digital Signal Processor), an ASIC (Application Specific Integrated Circuit), an FPGA (Field Programmable Gate Array) or other programmable logic devices, transistor logic devices, hardware components, or any combination thereof. It may implement or execute the various illustrative logical blocks, modules, and circuits described in connection with this disclosure. The processor 301 may also be a combination that implements computing functions, such as a combination of one or more microprocessors, a combination of a DSP and a microprocessor, etc.

The bus 402 may include a path for information transmission between the above-mentioned components. The bus 402 may be a PCI (Peripheral Component Interconnect) bus or an EISA (Extended Industry Standard Architecture) bus, etc. The bus 402 may include an address bus, a data bus, a control bus, etc. For ease of presentation, only one thick line is used in FIG. 8, but it does not mean that there is only one bus or one type of bus.

The memory 403 may be an ROM (Read Only Memory) or other types of static storage devices that can store static information and instructions, an RAM (Random Access Memory) or other types of dynamic storage devices that can store information and instructions, or it may also be, but not limited to, an EEPROM (Electrically Erasable Programmable Read Only Memory, a CD-ROM (Compact Disc Read Only Memory) or other optical disc memories (including compact discs, laser discs, optical discs, digital universal discs, Blu-ray discs, etc.), magnetic disk storage media or other magnetic storage devices, or any other medium capable of carrying or storing desired program code in the form of instructions or data structures that can be accessed by a computer.

The memory 403 is configured to store an application program code for executing the solution of the present application, and is controlled by the processor 401 for execution. The processor 401 is configured to execute the application program code stored in the memory 403 to implement the contents shown in the foregoing method embodiments.

The electronic device here includes but is not limited to: a mobile terminal such as a mobile phone, a laptop computer, a digital broadcast receiver, a PDA (personal digital assistant), a PAD (tablet computer), a PMP (portable multimedia player), and a vehicle-mounted terminal (such as a vehicle-mounted navigation terminal), and a fixed terminal such as a digital TV and a desktop computer. It may also be a serve or the like. The electronic device shown in FIG. 8 is only an example, and should not bring any limitation to the function and scope of use of the embodiments of the present application.

In another aspect, the present application provides a computer-readable storage medium. The computer-readable storage medium stores a computer program. When run on a computer, the computer can execute the corresponding content in the foregoing method embodiments. Compared with a prior art, in the embodiment of the present application, based on the cfDNA sequencing result of the biological sample and the multiple mutation markers, the filtering and screening is performed to determine a SNV/INDEL feature; based on the CNV baseline information and the genome of the biological sample, CNV feature obtaining is performed to obtain a CNV feature, and then the SNV/INDEL feature and CNV feature corresponding to the biological sample are integrated. Based on the feature combination, the urothelial carcinoma detection model is used for urothelial carcinoma screening to obtain a screening result. Use of the urothelial carcinoma detection model for cancer screening achieves non-invasive detection, and based on the SNV/INDEL feature and CNV feature corresponding to the biological sample, the accuracy of screening at an early stage for urothelial carcinoma is higher.

It should be understood that although the various steps in the flowcharts in the figures are displayed in sequence as indicated by arrows, these steps are not necessarily performed sequentially in the order indicated by the arrows. Unless explicitly stated in this article, the execution of these steps is not strictly limited in order, and they may be executed in other orders. Moreover, at least some of the steps in the figures may include multiple sub-steps or multiple stages. These sub-steps or stages are not necessarily executed at the same time, but can be executed at different time. These sub-steps or stages are not necessarily executed in sequence, but may be executed in turn or alternately with other steps or at least some of the sub-steps or stages of other steps.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1

Total 155 urothelial carcinoma samples and 150 healthy samples are divided into training and validation sets, and other 89 urothelial carcinoma samples and 157 samples from healthy people are considered as an independent test set. Each test sample in the training, validation and test sets is processed accordingly to obtain the corresponding feature combinations of all the test samples. Then, a logistic regression model prediction is performed based on all feature combinations corresponding to a large number of test samples. If the predicted value is greater than or equal to 0.5, the test sample status is determined to be positive. If the predicted value is less than 0.5, the test sample status is determined to be negative. The execution process for each test sample is shown in FIG. 5. In FIG. 5, the sample represents a test example, the SNV/INDEL and the CNV represent a SNV/INDEL feature and a CNV feature respectively, the mutation number represents the mutation number, the mutation label represents the label for mutation, the mutation max frequency represents maximum mutation frequency, CNV number represents the number of CNVs, the CNV label represents the label for CNV. Then, prediction is made on the basis of the logistic regression model to obtain the predicted value. If the predicted value is greater than or equal to 0.5, the test sample status is determined to be positive. If the predicted value is less than 0.5, the test sample status is determined to be negative.

In the meanwhile, the construction of a urothelial carcinoma detection model was carried out from three aspects: SNV/INDEL feature only, CNV feature only, and the combination of SNV/INDEL feature and CNV feature. In the operation of determining the CNV number in the CNV feature, it is determined on the basis of the combination of the first CNV number, the second CNV number, and the third CNV number, and the results shown in Tables 1 to 6 are obtained.

TABLE 1

| Performance of training and validation sets under SNV/INDEL feature | | | | |
|---|---|---|---|---|
| Type of data set | Number of samples from patients with urothelial carcinoma | Number of samples from healthy people | Sensitivity | Specificity |
| Training set | 84 | 90 | 61/84 = 0.726 | 90/90 = 1 |
| Validation set | 71 | 60 | 50/71 = 0.704 | 60/60 = 1 |
| Total | 155 | 150 | 111/155 = 0.716 | 150/150 = 1 |

TABLE 2

| | Performance of training and validation sets under CNV feature | | | |
| --- | --- | --- | --- | --- |
| Type of data set | Number of samples from patients with urothelial carcinoma | Number of samples from healthy people | Sensitivity | Specificity |
| Training set | 84 | 90 | 57/84 = 0.676 | 90/90 = 1 |
| Validation set | 71 | 60 | 49/71 = 0.690 | 59/60 = 0.983 |
| Total | 155 | 150 | 106/155 = 0.683 | 149/150 = 0.993 |

The CNV feature in Table 2 is determined on the basis of the first CNV number and the second CNV number.

TABLE 3

| | Performance of training and validation sets under CNV feature | | | |
| --- | --- | --- | --- | --- |
| Type of data set | Number of samples from patients with urothelial carcinoma | Number of samples from healthy people | Sensitivity | Specificity |
| Training set | 84 | 90 | 65/84 = 0.773 | 90/90 = 1 |
| Validation set | 71 | 60 | 54/71 = 0.760 | 58/60 = 0.967 |
| Total | 155 | 150 | 119/155 = 0.767 | 148/150 = 0.987 |

The CNV feature in Table 3 is determined on the basis of the first CNV number and the third CNV number.

TABLE 4

| | Performance of training and validation sets under CNV feature | | | |
| --- | --- | --- | --- | --- |
| Type of data set | Number of samples from patients with urothelial carcinoma | Number of samples from healthy people | Sensitivity | Specificity |
| Training set | 84 | 90 | 58/84 = 0.690 | 90/90 = 1 |
| Validation set | 71 | 60 | 54/71 = 0.760 | 58/60 = 0.967 |
| Total | 155 | 150 | 112/155 = 0.722 | 148/150 = 0.987 |

The CNV feature in Table 4 is determined on the basis of the second CNV number and the third CNV number.

TABLE 5

| | Performance of training and validation sets under CNV feature | | | |
| --- | --- | --- | --- | --- |
| Type of data set | Number of samples from patients with urothelial carcinoma | Number of normal-person samples | Sensitivity | Specificity |
| Training set | 84 | 90 | 60/84 = 0.714 | 90/90 = 1 |
| Validation set | 71 | 60 | 52/71 = 0.732 | 58/60 = 0.967 |
| Total | 155 | 150 | 112/155 = 0.722 | 148/150 = 0.987 |

The CNV feature in Table 5 is determined on the basis of the first CNV number, the second CNV number and the third CNV number.

TABLE 6

Performance of training set and validation set under
the combination of SNV/INDEL feature and CNV feature

| Type of data set | Number of samples from patients with urothelial carcinoma | Number of normal-person samples | Sensitivity | Specificity |
|---|---|---|---|---|
| Training set | 84 | 90 | 76/84 = 0.904 | 90/90 = 1 |
| Validation set | 71 | 60 | 65/71 = 0.915 | 58/60 = 0.967 |
| Total | 155 | 150 | 141/155 = 0.910 | 148/150 = 0.987 |

Referring to FIGS. 1-6, if based on the SNV/INDEL feature only, the urothelial carcinoma detection model has a sensitivity of 0.716 and a specificity of 1; if based on the CNV feature only, in a case where the CNV feature is determined on the basis of the first CNV feature and the second CNV feature, the urothelial carcinoma detection model has a sensitivity of 0.683 and a specificity of 0.993; in a case where the CNV feature is determined on the basis of the first CNV number and the third CNV number, the urothelial carcinoma detection model has a sensitivity of 0.767 and a specificity of 0.987; in a case where the CNV feature is determined on the basis of the second CNV number and the third CNV number, the urothelial carcinoma detection model has a sensitivity of 0.722 and a specificity of 0.987; in a case where the CNV feature is determined on the basis of the first CNV number, the second CNV number, and the third CNV number, the urothelial carcinoma detection model has a sensitivity of 0.832 and a specificity of 0.987. Therefore, in the case where the CNV feature is determined on the basis of the first CNV number, the second CNV number, and the third CNV number, the urothelial carcinoma detection model based on the CNV feature only has the best performance; and if based on the combination of SNV/INDEL feature and CNV feature, the urothelial carcinoma detection model has a sensitivity of 0.91 and a specificity of 0.98, achieving the best overall performance.

It can be seen that in the embodiment of the present invention, the corresponding cfDNA sequencing results of a large number of test samples are obtained, where a large number of test samples include a number of samples from healthy people and a number of samples from patients with urothelial carcinoma. For each test sample, the filtering and screening is performed on the basis of the cfDNA sequencing result of the test sample and multiple mutation markers to determine the SNV/INDEL feature; based on the CNV baseline information and the genome of the test sample, CNV feature obtaining is performed to obtain the CNV feature, and then the SNV/INDEL feature and CNV feature corresponding to the test sample are integrated to obtain a feature combination. Then, model training is performed on the basis of all feature combinations corresponding to a large number of test samples to obtain a urothelial carcinoma detection model. Training the model based on a large number of feature combinations can make the screening result more accurate during the screening based on the urothelial carcinoma detection model, that is, the sensitivity and specificity are both high.

Example 2

Total 148 mutation markers were obtained, comprising the 6 mutations from 3 genes of Table 7.

TABLE 7

Information of mutations

| Gene | chromosome | Start | End | Ref | Alt | c.HGVS | p.HGVS |
|---|---|---|---|---|---|---|---|
| TERT | chr5 | 1295228 | 1295228 | G | A | c.-124G > A | — |
| FGFR3 | chr4 | 1803564 | 1803564 | C | T | c.742C > T | p.R248C |
| TERT | chr5 | 1295250 | 1295250 | G | A | c.-146G > A | — |
| FGFR3 | chr4 | 1803568 | 1803568 | C | G | c.746C > G | p.S249C |
| ERBB2 | chr17 | 37868208 | 37868208 | C | T | c.929C > T | p.S310F |
| FGFR3 | chr4 | 1806099 | 1806099 | A | G | c.1118A > G | p.Y373C |

When using the listed 3 genes and 6 mutations, the detection performance is as shown in Table 8.

TABLE 8

Performance of training set and validation set under single SNV/INDEL features

| Type of data set | Number of samples from patients with urothelial carcinoma | Number of normal-person samples | Sensitiveness | specificity |
|---|---|---|---|---|
| Training set | 84 | 90 | 52/84 = 0.619 | 90/90 = 1 |
| Validation set | 71 | 60 | 43/71 = 0.605 | 60/60 = 1 |
| Total | 155 | 150 | 95/155 = 0.613 | 150/150 = 1 |

In the training set, there were a total of 84 pathologically positive samples, and 52 samples had one or more of the 6 mutations detected, with a sensitivity of 0.619. No mutations were detected in all 90 normal population samples, with a specificity of 1.

In the validation set, there were a total of 71 pathologically positive samples, and 43 samples had one or more of the 6 sites detected, with a sensitivity of 0.605. No mutations were detected in all 60 normal population samples, with a specificity of 1.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for detecting the presence of urothelial carcinoma, assessing the risk of urothelial carcinoma, and/or assessing the prognosis/progression of urothelial carcinoma in a subject, and treating the subject based on the detection and/or assessment, comprising:

a) obtaining sequence data of cell-free DNA (cfDNA) of a biological sample;

b) determining a single-nucleotide variation (SNV)/insertions/deletion (INDEL) feature of the biological sample based on the sequence data of cfDNA of the biological sample and a mutation marker, wherein the mutation marker is capable of distinguishing a subject without urothelial carcinoma from a subject with urothelial carcinoma; wherein, the SNV/INDEL feature comprises a mutation number, a mutation label, and/or a maximum mutation frequency, wherein, the mutation number is the number of the mutation marker in the biological sample, the mutation label is denoted 0 if the mutation number is 0, and the mutation label is denoted 1 if the mutation number is not 0, and, the maximum mutation frequency is the mutation frequency with the highest mutation frequency among more than one mutation markers in the biological sample;

c) obtaining a copy number variation (CNV) feature of the biological sample based on a CNV baseline information and a genome of the biological sample, optionally the CNV baseline is obtained from more than one samples from the healthy; wherein the CNV feature comprises a CNV number and/or a CNV label, wherein the CNV number is the number of positive markers among all chromosomes, and, the CNV label is denoted 0 if the CNV number is 0, and the CNV label is denoted 1 if the CNV number is not 0;

d) integrating the SNV/INDEL feature and the CNV feature of the biological sample to obtain a feature combination; and e) obtaining the result based on the feature combination using a model for urothelial carcinoma, wherein the model for urothelial carcinoma is obtained by training a logistic regression model using more than one training sets, validation sets and test sets, wherein the training sets, the validation sets and the test sets include a large number of samples from healthy subject and samples from a subject with a tumor, f) administering a therapeutic regimen selected from intravesical Bacillus Calmette-Guérin (BCG) therapy, chemotherapy, or cystectomy, based on the result obtained in step e), wherein b) comprises b1-1) obtaining a segment CNV score of more than one segments of the genome of the biological sample based on the CNV baseline information and the genome of the biological sample;

b1-2) determining a chromosome CNV score of each chromosome in the biological sample based on the segment CNV score;

b1-3) for the chromosome CNV score of each chromosome in the biological sample, comparing the absolute value of the chromosome CNV score and a first threshold; if the absolute value of the chromosome CNV score is greater than the first threshold, the CNV marker corresponding to the chromosome is determined to be a positive marker; if the absolute value of the chromosome CNV score is not greater than the first threshold, the CNV marker of the chromosome is determined to be a negative marker;

b1-4) obtaining a first CNV number, wherein the first CNV number is the number of positive markers among all chromosomes;

b1-5) determining the CNV feature based on the first CNV number.

2. The method of claim 1, wherein b) comprises:

b2-1) providing a tumor cell content of the biological sample, and b2-2) determining a second CNV number based on the relationship between the tumor cell content and a second threshold.

3. The method of claim 1, wherein b) comprises:

b3-1) for each segment of each chromosome in the biological sample, if the absolute value of the segment CNV score is greater than a third threshold, the segment is recorded as a CNV interval;

b3-2) for each chromosome in the biological sample, determining the feature ratio based on the CNV interval, wherein the feature ratio is the ratio of the length of all the CNV intervals to the length of the chromosome;

b3-3) for each chromosome in the biological sample, comparing the feature ratio and a fourth threshold, if the feature ratio is greater than the fourth threshold, the CNV mark is determined to be a positive mark, and if the feature ratio is not greater than the fourth threshold, the CNV mark is determined to be a negative mark;

b3-4) obtaining a third CNV number, wherein the third CNV number is the number of positive markers among all chromosomes.

4. The method of claim 2, wherein b1-5) comprises:

determining the CNV number based on the first CNV number and the target CNV number, wherein the target CNV number is the second CNV number and/or the third CNV number; and determining the CNV feature based on the CNV number.

5. The method of claim 1, wherein the b1-1) comprises:

determining a CNV score of each bin interval in the genome of the biological sample based on the CNV baseline information and the genome of the biological sample, wherein the CNV score is for reflecting the difference between the bin interval in the biological sample and the corresponding bin interval in the CNV baseline information; and merging the interval based on the CNV score of each bin interval in the genome of the biological sample to obtain the segment CNV score of multiple sections corresponding to the genome of the biological sample, wherein the section is obtained by continuous bin interval merging.

6. The method of claim 1, comprising providing the CNV baseline information before b), which comprises:

1) obtaining the genomes of more than one samples from the healthy;

2) for each sample from the healthy, conducting the CNV sliding window coverage calculation based on the genome of the sample from the healthy to obtain the read coverage of each bin interval in the genome of the samples from the healthy;

3) determining the CNV baseline information based on the read coverage of each bin interval, wherein the CNV baseline information comprises: the expected read coverage and the standard deviation of each bin interval, wherein, the expected read coverage is determined by averaging the read coverages of all samples from the healthy in each bin interval, and the read standard deviation is determined by calculating the variance of the read coverages of all samples from the healthy in each interval.

7. The method of claim 6, further comprising for each sample from the healthy, dividing the genome of the sample from the healthy into more than one bin intervals;

for each bin interval, collecting the sum of the number of reads whose start position or end position is located in the bin interval to obtain an initial read coverage of each bin interval;

for each bin interval, conducting GC correction and self-standardization based on the initial read coverage to obtain the read coverage of each bin interval in the genome of the sample from the healthy.

8. The method of claim 1, wherein the mutation marker is determined by filtering and screening mutation sites based on public tumor data, internal samples and sequencing data sets.

9. The method of claim 1, wherein the mutation marker comprising: a mutation of TERT, a mutation of FGFR3 and/or a mutation of ERBB2.

10. The method of claim 1, wherein the mutation marker is selected from the group consisting of: TERT chr5: 1295228-1295228, TERT chr5: 1295250-1295250, FGFR3 chr4: 1803564-1803564, FGFR3 chr4: 1803568-1803568, FGFR3 chr4: 1807890-1807890, FGFR3 chr4: 1807889-1807889, FGFR3 chr4: 1806099-1806099, FGFR3 chr4: 1806092-1806092, FGFR3 chr4: 1806089-1806089, and FGFR3 chr4: 1808937-1808937.

11. The method of claim 1, wherein the mutation marker comprises:

TERT chr5: 1295228-1295228, FGFR3 chr4: 1803564-1803564, TERT chr5: 1295250-1295250, FGFR3 chr4: 1803568-1803568, ERBB2 chr17: 37868208-37868208, and/or FGFR3 chr4: 1806099-1806099.

12. The method of claim 1, wherein the mutation marker comprises:

TERT c.-124G>A, FGFR3 c.742C>T, TERT c.-146G>A, FGFR3 c.746C>G, ERBB2 c.929C>T, and/or FGFR3 c. 1118A>G.

13. A device for detecting the presence of urothelial carcinoma, assessing the risk of urothelial carcinoma, and/or assessing the prognosis/progression of urothelial carcinoma, wherein the device is for conducting the method of claim 1.

* * * * *